(12) United States Patent
Blain et al.

(10) Patent No.: US 8,764,762 B2
(45) Date of Patent: *Jul. 1, 2014

(54) ATTACHABLE INSTRUMENT GUIDE WITH DETACHABLE HANDLE

(75) Inventors: Jason Blain, Encintas, CA (US); Greg Martin, Encintas, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/426,388

(22) Filed: Mar. 21, 2012

(65) Prior Publication Data

US 2013/0023889 A1 Jan. 24, 2013

Related U.S. Application Data (63) Continuation of application No. 12/176,137, filed on Jul. 18, 2008, now Pat. No. 8,172,854.

(60) Provisional application No. 60/950,801, filed on Jul. 19, 2007.

(51) Int. Cl.
  *A61B 17/58* (2006.01)
  *A61B 17/60* (2006.01)
  *A61F 2/00* (2006.01)

(52) U.S. Cl.
  USPC ............................. 606/96; 606/86 A; 606/99

(58) Field of Classification Search
  USPC ........ 606/96–99, 104, 279; 623/17.11–17.16; 81/478, 58, 59, 459, 124.6, 177.1, 81/177.85, 437, 177.9
  See application file for complete search history.

(56) References Cited

U.S. PATENT DOCUMENTS

| | | | |
|---|---|---|---|
| 2,466,023 A | 4/1949 | Griffin | |
| 5,425,490 A | 6/1995 | Goble et al. | |
| 5,676,666 A | 10/1997 | Oxland et al. | |
| 5,755,721 A | 5/1998 | Hearn | |
| 5,851,207 A | 12/1998 | Cesarone | |
| 6,235,034 B1 | 5/2001 | Bray | |
| 6,342,057 B1 | 1/2002 | Brace et al. | |
| 6,436,103 B1 | 8/2002 | Suddaby | |
| 6,524,312 B2 | 2/2003 | Landry et al. | |
| 6,960,216 B2 * | 11/2005 | Kolb et al. | 606/96 |
| 7,011,665 B2 | 3/2006 | Null et al. | |
| 7,278,997 B1 | 10/2007 | Mueller et al. | |
| 7,416,553 B2 | 8/2008 | Patel et al. | |
| 7,488,327 B2 | 2/2009 | Rathbun et al. | |
| 7,731,721 B2 | 6/2010 | Rathbun et al. | |
| 7,776,047 B2 | 8/2010 | Fanger et al. | |
| 7,935,123 B2 | 5/2011 | Fanger et al. | |
| 2002/0082606 A1 | 6/2002 | Suddaby | |
| 2004/0186482 A1 | 9/2004 | Kolb et al. | |
| 2007/0233150 A1 | 10/2007 | Blain et al. | |

\* cited by examiner

*Primary Examiner* — Andrew Yang
(74) *Attorney, Agent, or Firm* — Knobbe, Martens, Olson & Bear, LLP (57) ABSTRACT

An instrument guide with device coupler, a handle and one or more instrument guide lumens is detachably coupled to an orthopedic implant to facilitate drilling of the fastener holes or to facilitate insertion of self-tapping or self-dripping fasteners. The handle is preferably detachable to facilitate access to the instrument guide lumens. The device coupler detachably engages the implantable device and aligns the instrument guide lumens with the fastener openings on the device.

8 Claims, 10 Drawing Sheets

ATTACHABLE INSTRUMENT GUIDE WITH DETACHABLE HANDLE

CROSS-REFERENCE TO RELATED APPLICATIONS

The present application is a continuation of U.S. application Ser. No. 12/176,137, now U.S. Pat. No. 8,172,854, filed Jul. 18, 2008 which claims priority under 35 U.S.C. §119(e) to U.S. Provisional Application No. 60/950,801 filed on Jul. 19, 2007, the disclosures of which is incorporated by reference herein in its entirety.

BACKGROUND OF THE INVENTION

1. Field of the Invention

The invention relates generally to systems and methods for performing spinal fixation, specifically attachable instrument guides used for spinal orthopedic procedures.

2. Description of the Related Art

Advancing age, as well as injury, can lead to degenerative changes in the bones, discs, joints, and ligaments of the spine, producing pain and instability. Under certain circumstances, alleviation of the problems can be provided by performing spinal fusion. Spinal fusion is a surgical technique in which two or more vertebrae of the spinal column are fused together to eliminate the motion between the fused vertebrae. Spinal fusion is used to treat conditions where the spine exhibits instability. Spine instability may result from causes such as fracture, scoliosis, and spondylolisthesis, where one or more vertebrae move in a forward direction relative to the other vertebrae. Spinal fusion with discectomy is also performed for herniations of the discs. This surgery involves removal of the affected disc and fusion of the adjacent vertebrae. Traditionally, bone grafts have been used to fuse the vertebrae, but various types of vertebral implants have also been used.

The use of bone fixation systems for treating bone conditions is well established. For example, a bone plate may be positioned over and surrounding the bone injury area and secured to the bone. The bone plate can be secured to the bone by bone screws or other similar fasteners inserted through holes in the bone plate and into the bone itself, sometimes positioned with a drill guide. The screws are tightened so that the bone plate holds the bone to be treated in place in order to insure proper healing. Early fixation devices tended to be applicable only to long-bone injuries, with only limited uses for lower lumbar spinal injuries and disorders. The use of plate/screw fixation systems later expanded, however, to include uses for spinal injuries, including fusion of vertebrae and fixation devices for treating cervical vertebrae injuries.

SUMMARY OF THE INVENTION

A instrument guide comprising one or more instrument guide lumens, a handle, and a device coupler is disclosed. The handle is preferably detachable to facilitate access to the instrument guide lumens. The device coupler detachably engages the implantable device and aligns the instrument guide lumens with the fastener openings on the device. The instrument guide is preferably used with orthopedic applications, but may also be used in other surgical fields. Alternatively, the instrument guide may comprise an anatomical coupler configured to detachably engage the surrounding anatomical structures to secure the instrument guide to the implantation site.

In one embodiment, an instrument guide is provided, comprising a releasable lock assembly comprising a lumen; a shaft having a proximal end and a distal end, wherein the shaft is partially in the lumen of the releasable lock assembly; a handle at the proximal end of the shaft; a means for detachably coupling an implantable device; and at least one drill guide member joined to the means for detachably coupling an implantable device; wherein the releasable lock assembly is configured to releasably lock the distal end of the shaft and the means for detachably coupling an implantable device.

In another embodiment, an instrument guide is provided, comprising a releasable lock assembly comprising a lumen; a shaft having a proximal end and a distal end, wherein the shaft is partially in the lumen of the releasable lock assembly; a handle at the proximal end of the shaft; a device coupler comprising a coupling base with a through lumen and an elongate coupling member comprising a proximal end and a distal end, wherein the distal end is configured with a least one mechanical interfit structure, wherein at least a portion of the elongate coupling member is configured so as to move in the through lumen of the coupling base; and at least one drill guide member joined to the device coupler; wherein the releasable lock assembly is configured to releasably lock the proximal end of the elongate coupling member of the device coupler to the distal end of the shaft. The mechanical interfit structure may comprise helical threads. The releasable lock assembly may comprise an outer tubular member having a proximal end and a distal end. The instrument guide may further comprise at least one fixed coupling member extending from the coupling base. The distal end of the shaft may comprise a distal receiving lumen having a lumenal surface, an ablumenal surface, and a lock lumen between the lumenal surface and the ablumenal surface. The distal receiving lumen of the shaft may comprise a non-circular cross-sectional shape. The proximal end of the elongate coupling member may have a configuration that forms a mechanical interfit with the distal receiving lumen of the shaft. The lock lumen may have a luminal opening and an ablumenal opening. The luminal opening of the lock lumen may have at least one dimension that is smaller than the ablumenal opening of the lock lumen. The releasable lock assembly may further comprise a movable lock element having a locking position wherein the lock element protrudes through the lumenal opening and a releasing position wherein the lock element does not protrude through the lumenal opening. The lumen of the releasable lock assembly may have an enlarged cross-sectional area about the distal end of the shaft. The lock element may be a ball bearing. The instrument guide may further comprise a bias member within the distal receiving lumen of the proximal tubular shaft. The bias member may be configured to bias the lock element in the lock position. The coupling base comprises a distal concave surface. The shaft and the releasable lock assembly may be configured to permit at least some relative rotational movement between the shaft and the releasable lock assembly. The shaft and the releasable lock assembly may be configured to permit at least some relative axial movement between the shaft and the releasable lock assembly. The instrument guide may further comprise a distal tubular shaft joined to the coupling base, the distal tubular shaft having a proximal end, a distal end and a lumen therebetween in which at least a portion of the elongate coupling member movably resides. The elongate coupling member may have a proximal position and a distal position. The instrument guide may further comprise a distal bias member between a surface of the elongate coupling member and a surface of the distal tubular shaft. The distal bias member may be configured so as to bias the elongate coupling member to the proximal position. The distal bias member may be configured so as to bias the elongate coupling member to the distal position.

In another embodiment, a method for treating a patient is provided, comprising attaching an instrument guide with respect to an implantable device, wherein the instrument guide comprises a detachable handle and at least one instrument guide lumen; inserting the implantable device to an implantation site; separating the handle from the instrument guide; passing a component through the at least one instrument guide lumen to the implantable device to the implantation site; reattaching a handle to the instrument guide; and releasing the instrument guide with respect to the implantable device. Attaching the instrument guide to the implantable device may occur after inserting the implantable device to the implantation site. The implantation site may be an intervertebral space. The implantable device may be an interbody fusion implant, preferably a flanged interbody fusion implant. The component passed through the at least one instrument guide lumen may be selected from a group consisting of a drill, a fastener and a screw driver.

All of these embodiments are intended to be within the scope of the invention herein disclosed. These and other embodiments will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

These and other features, aspects, and advantages of the invention disclosed herein are described below with reference to the drawings of preferred embodiments, which are intended to illustrate and not to limit the invention.

DETAILED DESCRIPTION OF THE PREFERRED EMBODIMENT

Although certain preferred embodiments and examples are disclosed below, it will be understood by those in the art that the invention extends beyond the specifically disclosed embodiments and/or uses of the invention and obvious modifications and equivalents thereof. Thus, it is intended that the scope of the invention herein disclosed should not be limited by the particular disclosed embodiments described below.

Devices such as bone plates, implants, and other orthopedic devices can be secured to a bone using bone screws or other bone fixation members inserted through the device. The insertion of the bone screws may be directed by an instrument guide for more precise placement, especially for surgical sites with limited access or visibility, such as the cervical spine. Although some instrument guides may be referred to as drill guides, instrument guides need not be used with actual drills but can be used for insertion of self-tapping or self-drilling fasteners, or to generally provide a guided pathway to a particular location for any of a number of purposes. For example, an instrument guide can also facilitate access to the fastener aperture and/or bone to perform a bone biopsy or for injection of drugs, cements or radiographic products.

A drill guide typically comprises a drill guide lumen mechanically coupled to a shaft, which is mechanically coupled to a handle. The handle provides added maneuverability such that the user may position the drill guide lumen more accurately. Many drill guides, however, must be held steady by the user during the drilling process. An instrument guide that can detachably engage the implantable device or the surgical site may facilitate implantation by not requiring holding during the instrumentation process. An attachable instrument guide may also be useful for manipulating implantable devices that are small in size or difficult to access, by providing a larger structure for the user to manipulate during implantation, which can then be detached once implantation is completed.

Figure 1:
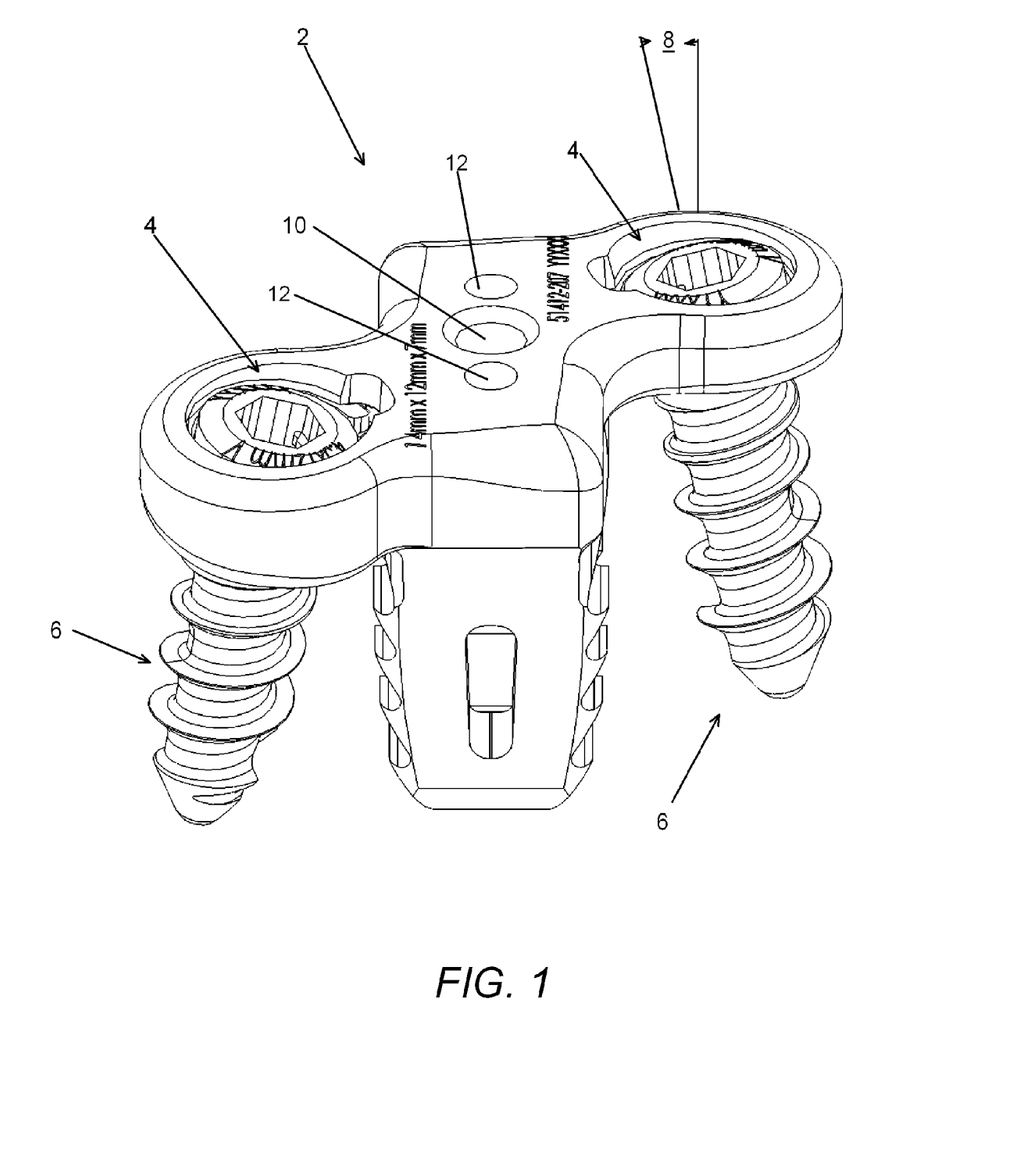
FIG. 1 is a perspective view of a flanged interbody fusion implant.

Referring to FIG. 1, one example of a device that may be used in conjunction with an instrument guide is a flanged interbody fusion implant 2. An instrument guide can facilitate access to the fastener apertures 4 of the implant 2, as well as provide a guide for a particular angle of access to the apertures. This latter function may be particular useful for both devices with fixed angle fastener configurations and those with polyaxial fastener configurations. For fixed angle devices, providing the correct drilling or insertion angle for the fastener 6 provides a more stable fit between the fastener 6 and the fastener aperture 4. For polyaxial devices, an instrument guide can facilitate the correct drilling or insertion angle of the desired fixation angle 8 between the polyaxial fastener 6 and the screw apertures 4 of the implant 2. To facilitate attachment or engagement of an instrument guide to an implant 2, the implant may further comprise one or more attachment sites to facilitate the attachment and/or detachment of the instrument guide. In the particular embodiment depicted in FIG. 1, the implant 2 comprises coupling openings 10, 12. As depicted, the openings 10, 12 are generally of circular shape, varying diameter, and depth, but in other embodiments, different shapes, diameters and/or depths, locations or numbers of holes may be used. The coupling openings 10, 12 may have a similar configuration while other holes may have different configurations. The attachment structures need not be located centrally or symmetrically on the device. In other embodiments, the implantable device may comprise attachment structures that protrude from the surface of the implant, such as a flange.

Figure 2A:
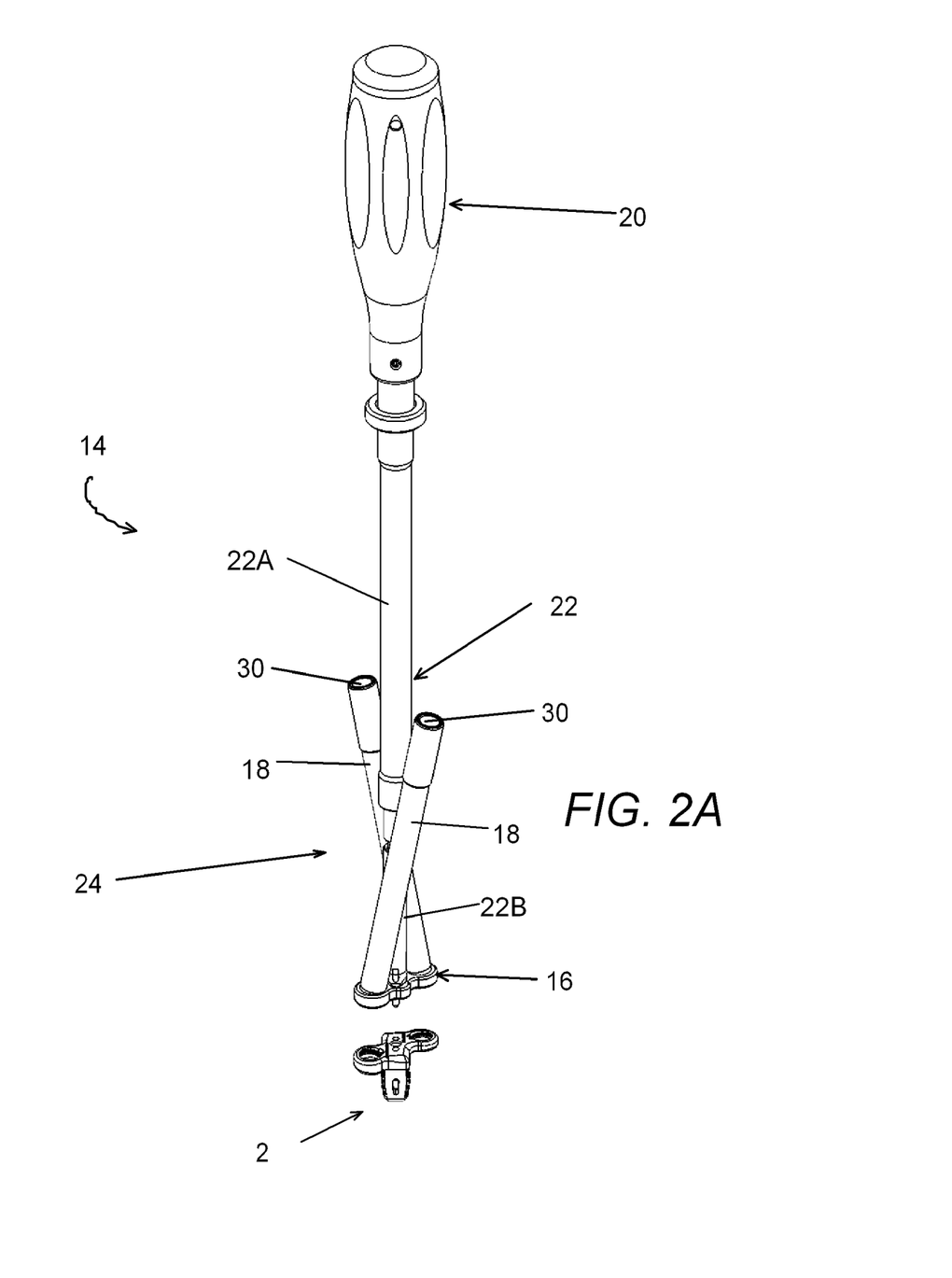
FIG. 2A depicts a perspective side view of one embodiment of an instrument guide that may be used with the flanged interbody fusion implant in FIG. 1.
Figure 2B:
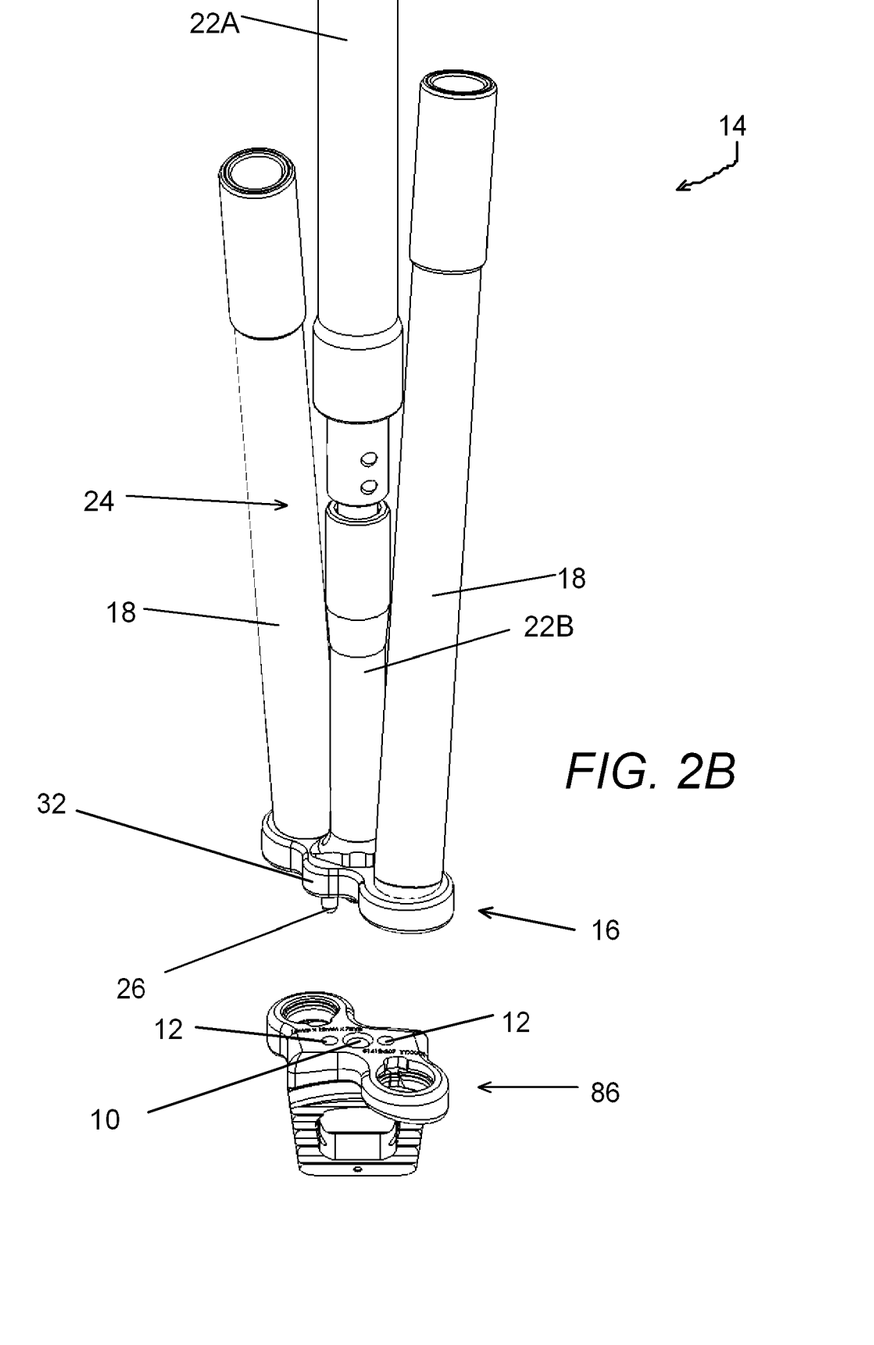
FIGS. 2B and 2C are detailed bottom perspective and elevational views of the flanged interbody fusion implant and the distal end of the instrument guide of FIG. 2A, respectively.
Figure 2C:
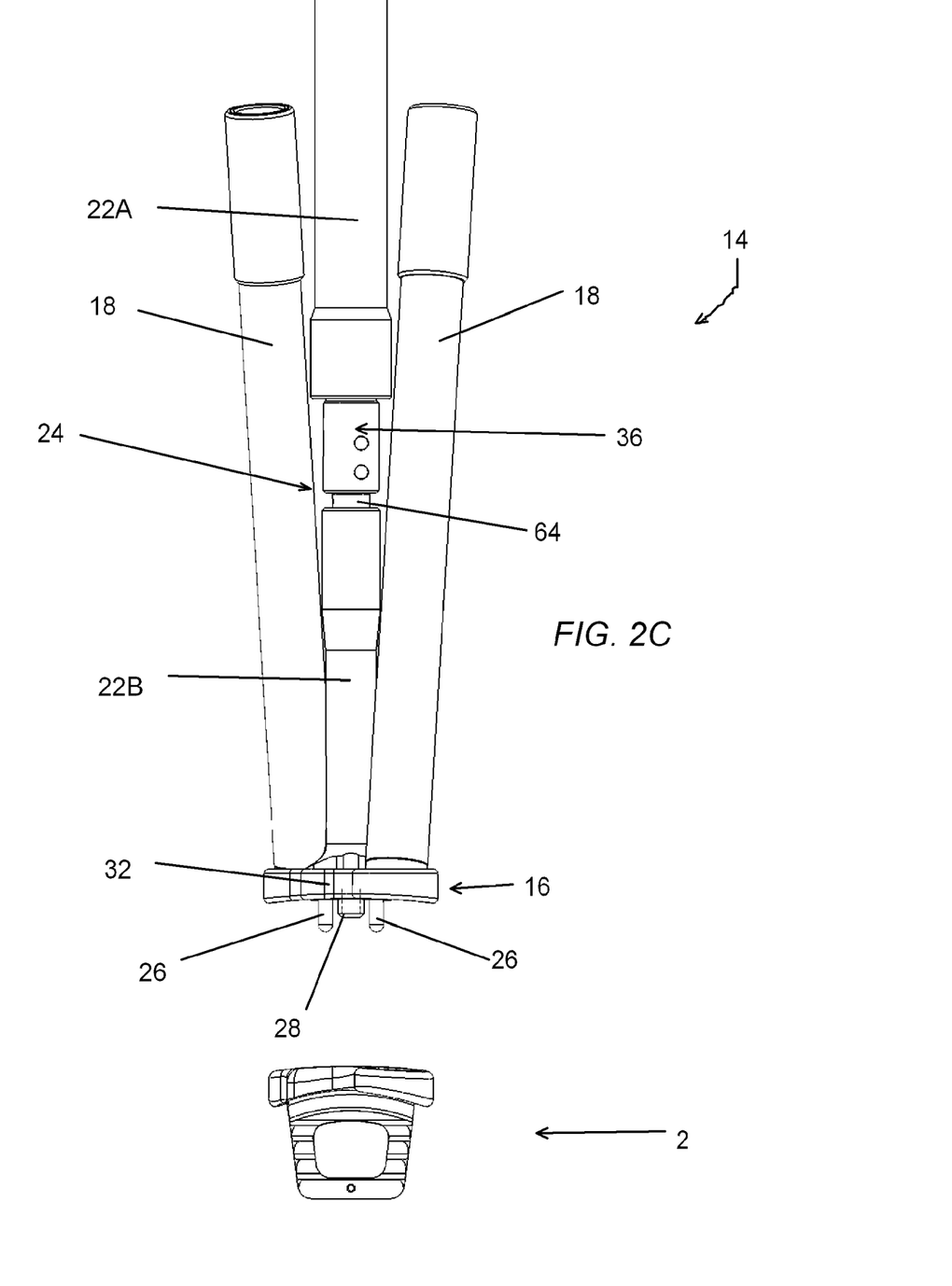

As shown in FIGS. 2A to 2C, in one embodiment of the invention, the instrument guide 14 comprises one or more guide members 18 and a device coupler 16 with one or more coupling structures 26, 28 engageable to the implant 2. The instrument guide 14 further comprises a handle 20 and a handle shaft 22 comprising a detachable proximal shaft 22A and a distal shaft 22B attached to the device coupler 16. An engagement assembly 24 between the proximal shaft 22A and distal shaft 22B facilitates attachment and detachment of the proximal shaft 22A and handle 20 from the rest of the guide device 14, and also provides a mechanical interlink between the handle 20 and the device coupler 16 to control coupling and decoupling of the implantable device 2. In other embodiments of the invention, the handle 20 may be permanently attached rather and an engaging assembly 24 is not provided.

In embodiments comprising a detachable handle 20, the relative lengths between the proximal shaft 22A and the distal shaft 22B can vary. In some embodiments, the engagement assembly 24 may be located on the device coupler 16 such that a distal shaft 22B is not provided. In embodiments comprising a distal shaft 22B, longer distal shafts 22B may be easier to engage than shorter distal shafts 22B, depending upon the lengths of the guide lumens 18. Preferably, the length of distal shaft 22B is shorter than the lengths of the guide lumens 18, to reduce interference from distal shaft 22B with use of the guide lumen 18 when proximal shaft 22A is detached from distal shaft 22B.

Figure 3A:
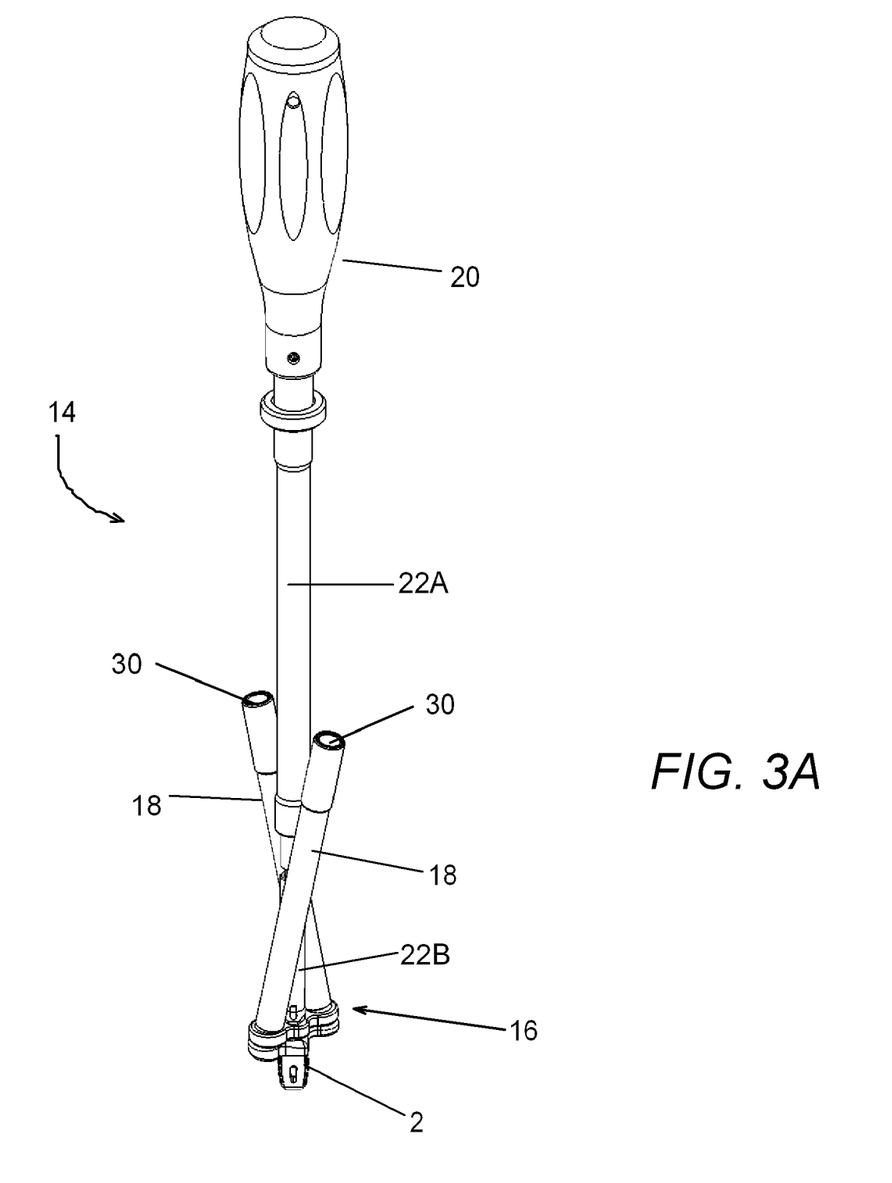
FIG. 3A is a perspective side view of the instrument guide in FIG. 1 contacting but not engaged to the flanged interbody fusion implant.
Figure 3B:
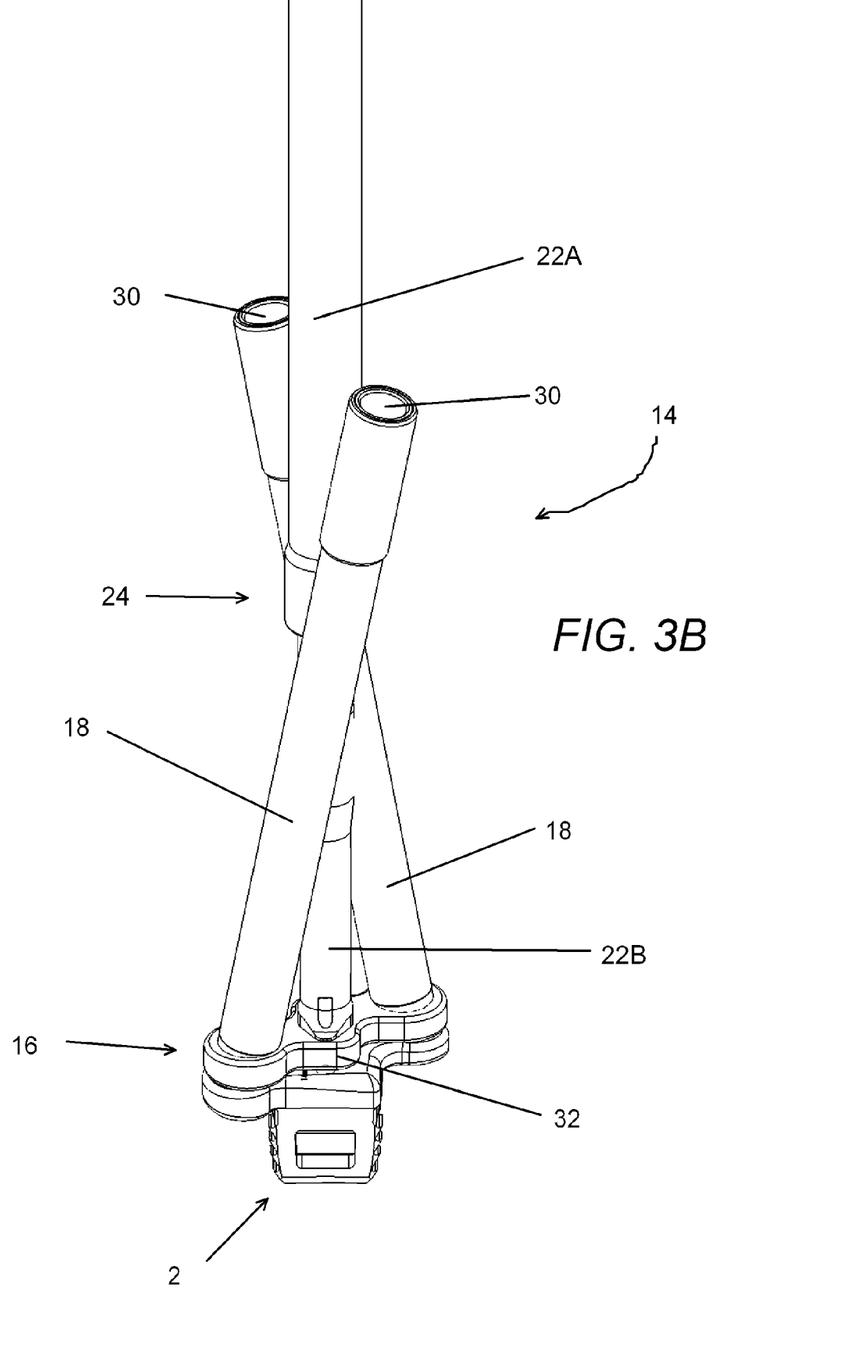
FIG. 3B is a detailed bottom perspective view of the instrument guide and the flanged interbody fusion implant of FIG. 3 after coupling.

In FIGS. 2B and 2C, the implantable device 2 and the instrument guide 14 are illustrated in alignment in preparation for coupling. One or more fixed coupling members 26 are in alignment with the coupling openings 12 on the device 2, while one or more movable coupling member 28 are in alignment with the coupling opening 10 on the device 2. As can be appreciated by one skilled in the art, the number and configurations of the coupling members 26, 28 provided on the device coupler 16 can vary according to the particular implantable component. In some embodiments, all of the coupling members may have a movable configuration. In other embodiments, all of the coupling members may have a fixed configuration. FIGS. 3A and 3B depict the instrument guide 14 at least partially coupled to the implant 2. The aligned coupling between the instrument guide 14 and implant 2 matches the guide lumens 18 of the instrument guide 14 with the fastener apertures 4 of the implant 2.

Although the coupling members 26, 28 depicted in FIG. 2C are elongate members configured to insert into lumen-type coupling sites 10, 12 of the implant 2, in other embodiments the coupling members 26, 28 may be located on the implant 2 and the coupling openings 10, 12 may be provided on the instrument guide 14. In further embodiments, one or more coupling members 26, 28 may be removable from the coupling device 16 such that the coupling members may be removed, replaced, or substituted, depending upon the particular configurations of the devices being implanted.

Preferably, the movable coupling member 28 of the instrument guide 14 comprises a locking configuration or structure to detachably engage the implant 2. The locking or coupling mechanism on a movable coupling member 28 may comprise, for example, any of a variety of complementary mechanical interfits with the coupled implant, such as a threaded lock, snap-on fitting, or an interlocking fit. In other embodiments, the interfit may be a friction fit or a magnetic fit. In a preferred embodiment, the movable coupling member 28 comprises a threaded surface that engages a corresponding threaded lumen on the implant 2. In some embodiments, in order to bring the corresponding threaded surfaces together, the movable coupling member 28 may be axially movable from a retracted position to an extended position. The movable coupling member 28 may be movable longitudinally and rotationally until contact is made with the complementary coupling opening 10 on the implant 2, and then the movable coupling member 28 is rotatably threaded into the coupling opening 10 on the implant 2. The movable coupling member 28 may be freely positionable from its disengaged position to its engaged position, or the movable coupling member 28 may be biased by a spring or other bias member in either position and to provide tactile feedback to the user as to the current state between the delivery tool and the implant(s).

The fixed coupling structures 26 are configured and positioned to insert into the coupling sites 12 on the implantable device 2. In certain embodiments, the fixed coupling structures 26 serve to limit rotational movement between the implantable device 2 and the instrument guide 14, either during insertion of the implant 2, or during coupling between the implant 2 and the instrument guide 14 where the two components are coupled by a threaded interface.

Although the fixed coupling members 26 are located at equal distances on opposite sides from the movable coupling member 28, the coupling members 26, 28 need not be configured to be equal in size in shape or to be symmetric with respect to a central plane or central axis of any of the implantable components or the delivery tool. In other embodiments, one or more coupling members may have a cross-sectional shape that resists rotation in a complementary shaped recess on the implant, e.g. a polygonal or oval shape. The coupling members 26, 28 may be configured with a corresponding shape, depth, spacing, and size to fit with the complementary coupling sites 10, 12 of the implant 2.

In other embodiments, instead of a threaded movable coupling member 28, the coupling member may have a configuration that forms another type of mechanical interfit with the coupling opening 10 of the implant 2. In some embodiments, the movable coupling member 28 may comprise a hook that engages a recess or pin on the implantable device, or a pivot or clamp member that retain the components by grasping onto the sides of the components. As mentioned above, in some embodiments, the locking or coupling mechanism may be configured to generically couple devices of a general size or shape and need not be specifically configured to the delivery tool. One of skill in the art will understand that any of a variety of disengageable mechanisms known in the art may be used to detachably couple one or more implantable devices.

Figure 4:
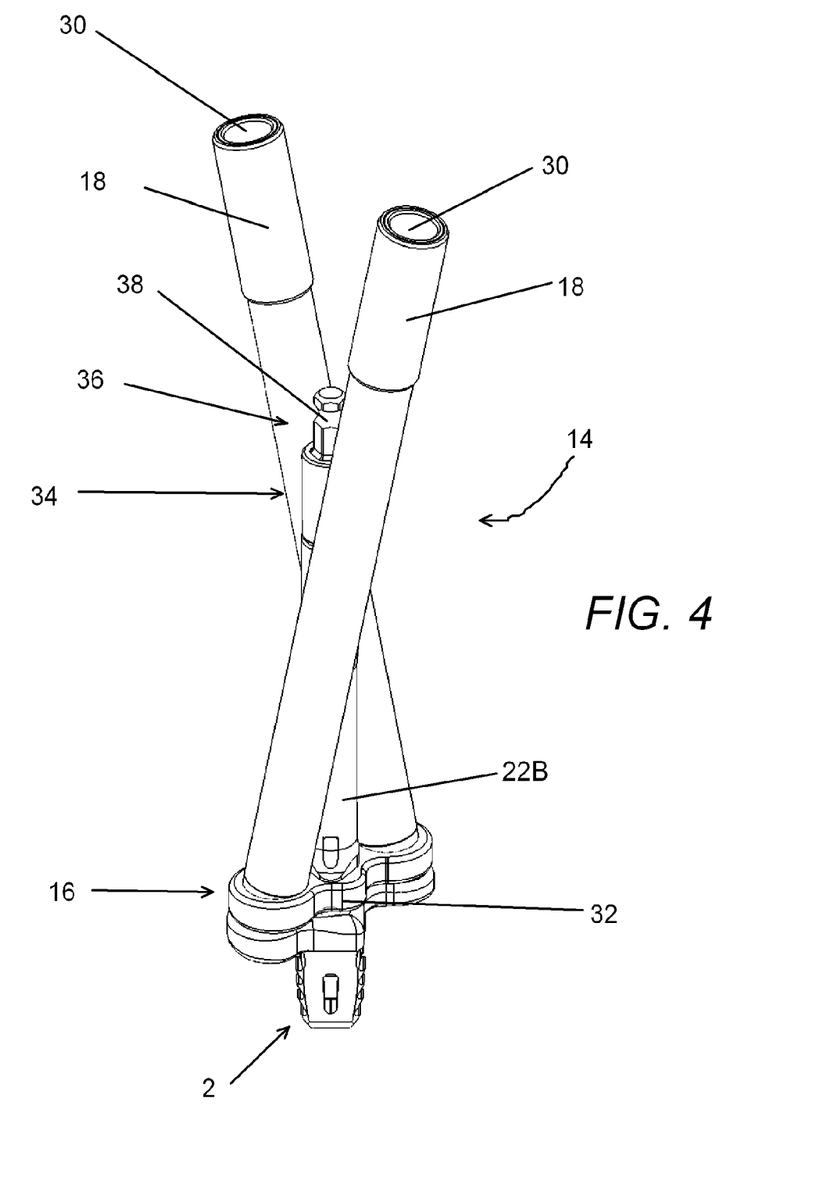
FIG. 4 is a perspective side view of the instrument guide and the flanged interbody fusion implant of FIG. 3B with the handle removed.

FIG. 4 depicts the instrument guide 14 coupled to the implant 2, but with the handle 20 and proximal shaft 22A removed. The proximal end 34 of the distal shaft 22B comprises an engagement member 36. The engagement member 36 comprises a recess or groove 38 to permit the distal engagement member 36 to be retained by a complementary proximal engagement structure in the distal end of the proximal shaft 22A. Details of the engagement assembly 24 and the mechanical linkage from the handle 20, through the distal engagement member 36 and to the movable coupling member 28 of the instrument guide 14 is described in greater detail below.

Figure 5:
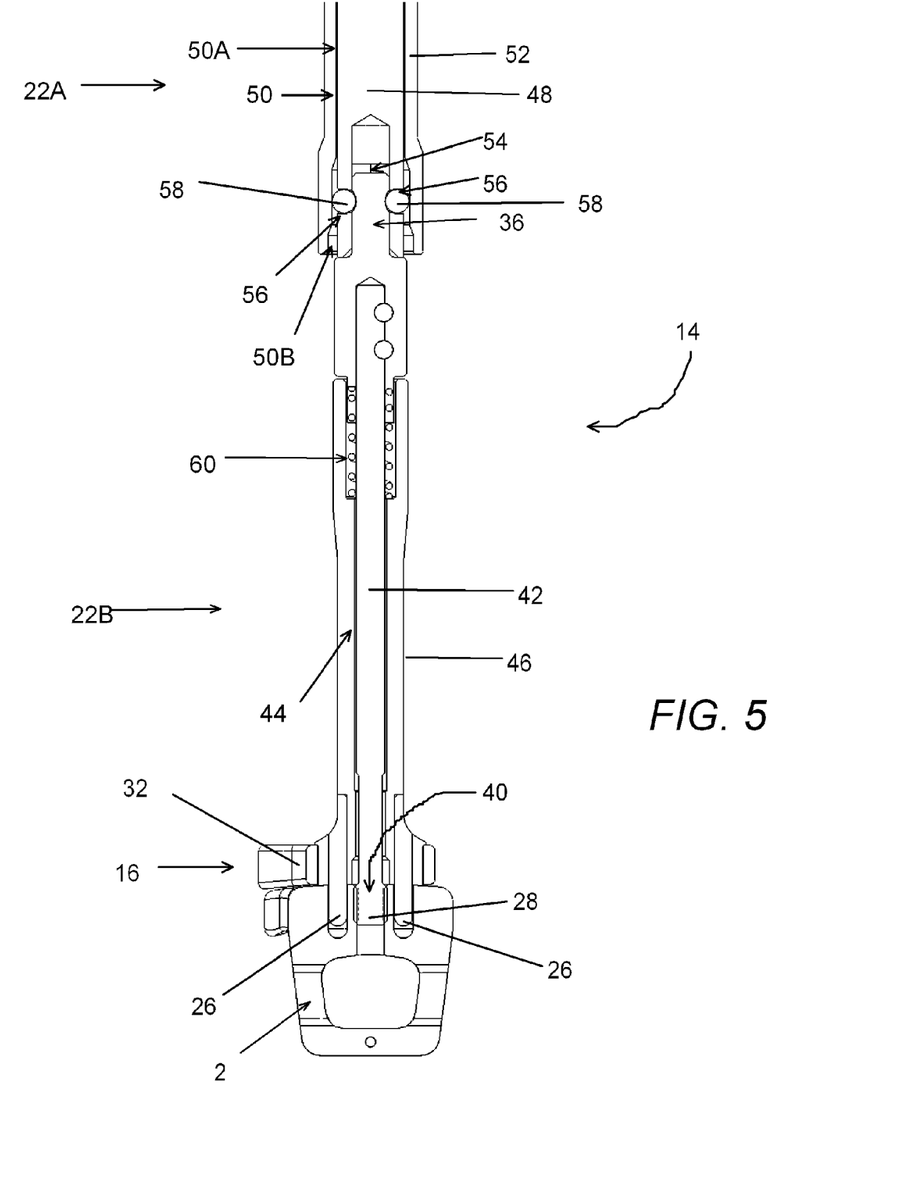
FIG. 5 is schematic cross-sectional view of the instrument guide and the flanged interbody fusion implant of FIG. 4.

FIG. 5 is a cross-sectional longitudinal view of the proximal and distal shafts 22A, 22B attached together and where the coupling device 16 is fully coupled to the implant 2. The movable coupling member 28 is the distal end 40 of a distal inner shaft 42 within a distal tubular lumen 44 of the distal outer shaft 46 of distal shaft 22B. The proximal shaft 22A comprises a proximal inner shaft 48 within the proximal tubular lumen 50 formed by a movable outer shaft 52. The proximal inner shaft 48 comprises a complementary engagement opening 54 configured to detachably retain the distal engagement member 36 of the distal shaft 22B. The proximal inner shaft 48 may further comprise one or more apertures 56 which contain one or more ball bearings 58 or other interference structures which can be displaced into the recess 38 of distal engagement member 36 to lock the proximal inner shaft 48 and the distal engagement member 36 together. The ball bearing(s) 58 can be maintained in the recess 38 of the distal engagement member 36 by the narrower lumen portion 50A of the proximal outer shaft 52, but is permitted to separate from the recess 38 by moving the outer sleeve 52 of the shaft 22A proximally to its wider lumen portion 50B. One of skill in the art will understand that any of a variety of detachable engagement interfaces may be used between the two shaft components, and that in some embodiments, the complementary engagement structures on the ends of each shaft member may be swapped.

The movable coupling member 28 is configured with a first axial position relative to the coupling base 32 and a second axial position relative to the coupling base 32. The movable coupling member 28 comprises an elongate member movable within a lumen 44 formed by the outer sleeve 46 of the lower shaft 22B. In some embodiments, the movable coupling member 28 is moved between the first axial position and the second axial position by using the handle 20 to cause axial translation of the distal engagement member 36. This occurs through the proximal inner shaft 48, the distal inner shaft 42 and the engagement assembly 24 that mechanically couples the two inner shafts 42, 48. The instrument guide 14 may be biased toward either the first axial position or the second axial position by one or more springs 60 or other bias members disposed within the shaft 22. The force required to move the distal inner shaft 42 against the resistance of the spring 60, may be varied to provide the desired degree of tactile response, or to facilitate the separation of the implant 2 when the movable coupling member 28 disengages from the coupling aperture 12. Any suitable degree of force or motion may be used.

A spring 60 or other bias member can facilitate separation of the movable coupling member 28 from the implantable device 2 by causing immediate additional retraction the movable coupling member 28 the moment the threaded interface is disengaged between the two components. This configuration can also provide visual indicators of engagement and disengagement between the instrument guide 14 and the implant 2. Referring to FIG. 2C, for example, the position of the movable coupling member 28 can be determined by the user based upon the gap 64 between the distal engagement member 36 and the proximal end 14B of the distal shaft 12B. Other indicia or indicator structures for determining the engagement or locking status between the instrument guide 14 and the implant 2, whether mechanical or electronic, may be used for this and other embodiments of the engaging structures and are well known in the art.

In other embodiments, a non-biased interface, such as a threaded interface or a sliding/twisting interlocking interface, for example, between the distal inner shaft 42 and the distal outer shaft 46 of the lower shaft 22B. For example, a handle motion that rotates the distal engaging member 36 can be configured to radially thread the movable coupling member 28 into a corresponding coupling recess 12 on the implant 2. In still other embodiments, the movable coupling member 28 may rotate but is not configured to retract or extend relative to the base 32 of the device coupler 16.

Referring back to the embodiment in FIG. 5, in embodiments where the distal inner shaft 42 is configured to rotate in order to engage or disengage the implant 2, the distal engagement member 36 may be provided with an angled outer surface 62 or other non-circular cross-sectional shape so as to permit transmission of rotational force between the proximal inner shaft 48 and the distal inner shaft 42 in combination with the complementary shaped engagement opening 54 of the proximal shaft 22A.

In embodiments comprising a movable coupling member 28, as shown in FIG. 5, the fixed coupling members 26, if any, are preferably but not necessarily longer than the shortest extended position of the fixed coupling member 26, to resist rotational movement of the implant 2 even before the movable coupling member 26 contacts the implant 2 to initiate screwing of threading. The length of the fixed coupling members 26 help to stabilize the relative position between the instrument guide 14 and the implant 2 as the movable coupling member 26 engages the implant 2.

Referring back to FIGS. 2A to 2C, in certain embodiments, the guide members 18 each include a proximal opening 30, distal opening (not shown) accessible through the device coupler 16, and a lumen therebetween. The guide members 18 may comprise any shape suitable for accurately guiding a drilling device or other instrument, or fastener. The guide members 18 may have a tubular or trough-like configuration and may be linear or non-linear. Non-linear guide members may facilitate access to difficult anatomical sites. Non-linear or flexible drills, screw drivers and other tools are known in the art and may be used with the non-linear guide members.

Although FIGS. 2A to 2C depict two guide tubes 18 corresponding to the two fastener apertures 4 on the implant 2, the instrument guide 14 may comprise fewer or greater number of guide tubes 18 than the access sites on implant 2. In one example, an instrument guide with four guide tubes may be provided but used with interbody fusion devices or vertebral plates have the same or different number of fastener apertures. In some embodiments where the instrument guide has a fewer number of guide tubes than the implantable device 2, the device coupler may be rotatable to permit repositioning of the guide tubes with requiring detachment of the instrument guide from the implant 2. The instrument guide and the implant may be configured to facilitate alignment between the two components. In still other embodiments, for example where the implant 2 is a spinal implant that spans multiple vertebrae, the implant 2 may be provided with multiple sets of coupling sites 10, 12 so that a single instrument guide can be attached and detached for use at different sites on the implant 2.

In addition to the cylindrical guide lumens illustrated in FIGS. 2A to 2C, non-cylindrical configurations are also contemplated, including non-circular tubular lumens, frustoconical lumens, and others. The guide lumens 18 need not be circumferentially enclosed, and in some embodiments may have a trough-like configuration or have a seam along the length of the guide lumen 18. Although cylindrical guide lumens are preferred, non-cylindrical configurations are also contemplated, including non-circular tubular lumens, frustoconical lumens, and others.

Figure 6A:
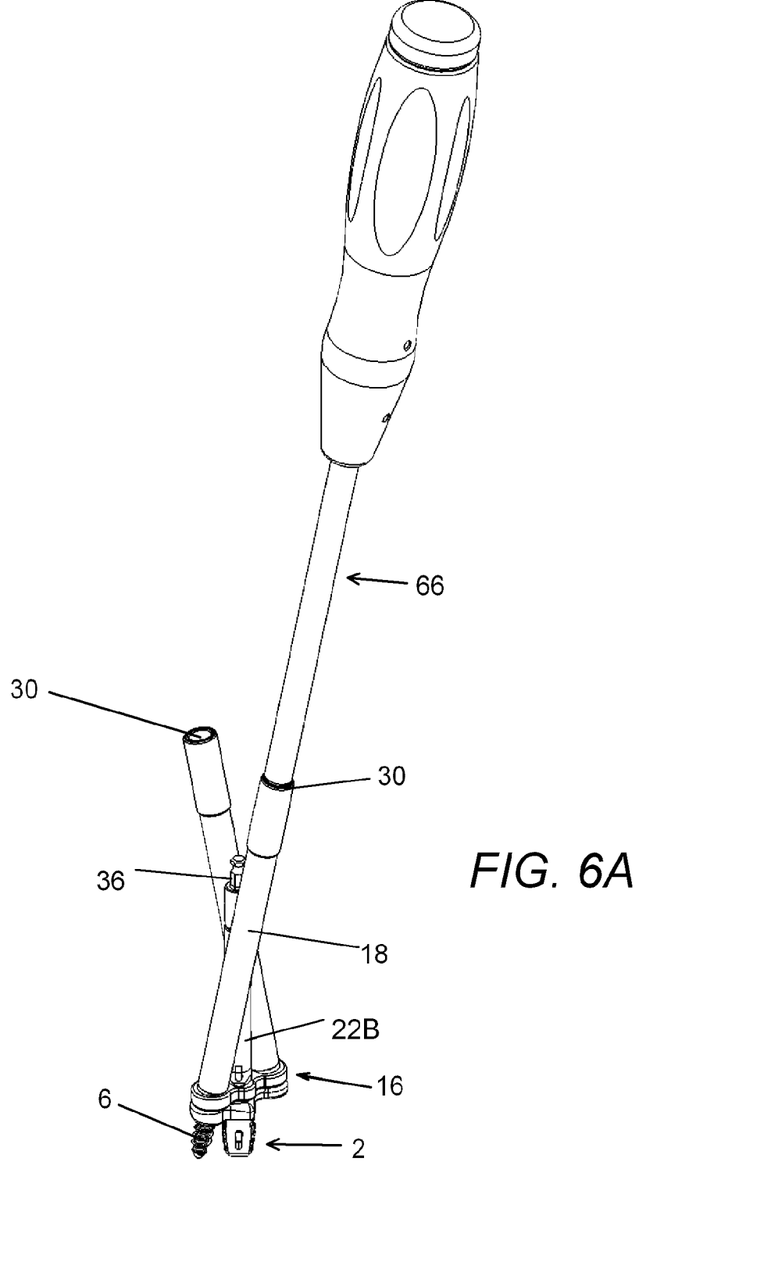
FIGS. 6A and 6B are schematic perspective side views of the insertion of the first and second bone screws, respectively, with a screw driver.
Figure 6B:
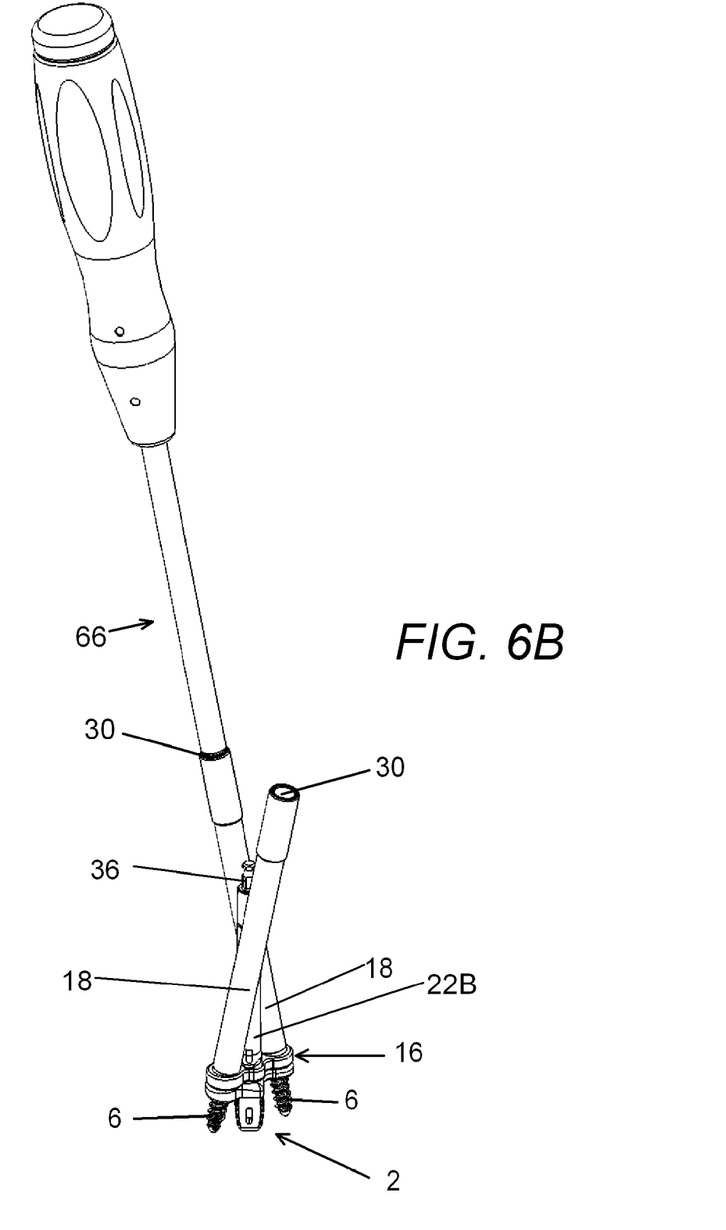

FIGS. 6A and 6B are perspective views of the guide tool 14, with the handle 20 and proximal shaft 22A detached from the distal shaft 22B. This permits the user to insert instruments or fasteners into the guide tubes 18 without potential interference from the protruding handle 20. After the implant 2 is positioned in its desired location and orientation, self-tapping or self-drilling bone fasteners 6 may be inserted into the proximal openings 30 of the guide tubes 18 and fastened to bone using a screw driver 66. When attachment of the implant 2 is complete, the handle 20 and proximal shaft 22A is reattached to the distal engagement member 36 to detach the instrument guide 14 from the implant 2. In the embodiment depicted in FIG. 5, the proximal outer shaft 52 is retracted relative to the handle 20 and inner proximal shaft 48, thereby permitting the ball bearings 58 to displace outward into the larger lumen section 50B of the proximal tubular lumen 50 as the distal engagement member 36 is inserted into the complementary engagement opening 54. Once the distal engagement member 36 is fully inserted, the proximal outer shaft 52 is extended to lock the bearings 58 into the groove or recess 38 by limited displacement of the ball bearing 58 using the narrow lumen 50A.

In some embodiments of the invention, the device coupler 16 may have multiple lower shafts 22B, which may be similar or different in location or length. It may be beneficial to provide additional engagement sites for the handle 20 during procedures from multiple different access pathways which may be limited in number if only a single handle attachment site is provided. In some embodiments, the engagement sites for the handle 20 may be different.

In one example, the proximal shaft 22A is configured to couple to either the distal shaft 22B or a guide tube 18. The proximal shaft 22A may be configured with two mechanical coupling mechanisms. This is advantageous for procedures where the user initially couples the proximal shaft 22A to the distal shaft 22B to provide more precise control for initially positioning the instrument guide 14 at a desired target location. The proximal shaft 22A is subsequently attached to a guide member 18 to help stabilize the implant during fastener insertion or drilling. The attachment to the guide member 18 may occur by a different mechanism than the attachment of to the distal shaft 22B of the device coupler 16. For example, complementary threaded surfaces may be used between the proximal shaft 22A of the handle 20 and the distal shaft 22B of the device coupler 16. As will be appreciated, the order of the attachment and detachment of the proximal shaft 22A to a distal shaft 22B or a guide member 18 may vary, depending on the nature and complexity of the procedure.

Although the guide members 18 of the instrument guide 14 are preferably fixed to the device coupler 16, in some embodiments, the guide members 18 may be lockably movable or removable. The base 32 of the device coupler 16 can be configured, for example, to receive both an instrument guide assembly with two or more instrument guide members arranged in one configuration and a drill guide assembly with two or more drill guide lumens arranged in another configuration. Suitable assemblies, such as threading, snap-on fittings and lockable hinge joints, are well-known in the mechanical arts.

In other embodiments of the invention, one or more movable joints may be provided between the base 32 of the device coupler 16 and the handle 20, to allow the drill guide 14 to be held in different positions and improve the visibility of the surgical site or the direction from which the user is holding the drill guide 14. The joints may be any of a variety of joints or linkages known in the art, including but not limited ball-and-socket, hinge, and axle joints. The joints are preferably but not required to be lockable in one or more positions. Some embodiments of the invention have movable handles such as those disclosed in U.S. application Ser. No. 11/693,145, filed Mar. 29, 2007, and entitled "DRILL GUIDE WITH ROTATING HANDLE", which is attached herewith as an appendix. Other handle and shaft embodiments are also contemplated, including a telescopic handle shaft.

In one embodiment of the invention, a method of coupling an orthopedic device to a drill guide 14 is provided, comprising positioning the fixed coupling members 26 and the movable coupling members 28 of a device coupler 16 axially over the coupling sites 10, 12 of one or more devices 2, inserting the coupling member 26, 28 into the corresponding coupling sites 10,12 of the device 2, and moving the handle 20 from a first position to a second position to couple the movable coupling member 28 to the corresponding coupling site 12.

Coupling the instrument guide 14 and device coupler 16 to the orthopedic device 2 may comprise providing a drill guide 14 having an shaft 18 coupled to an device coupler 16, positioning the coupled device coupler 16 over the orthopedic device 2, positioning the prongs 26 in alignment with the engaging portion 12 of the orthopedic device 2, fitting the prongs 26 into the corresponding receiving areas of the orthopedic device 2, and moving the first 22A and second 22B shafts from the first position to a second locking position.

The instrument guide 14 may be attached to the orthopedic device 2 after initial positioning of the orthopedic device in the body. In a preferred embodiment, however, the instrument guide 14 is attached to the orthopedic device 2 prior to implantation, and the instrument guide 14 is also used as a delivery instrument used to insert and fix the orthopedic device 2 to the spine. In this preferred embodiment, only a single attachment and a single detachment step is used to implant the orthopedic device 2, which simplifies the implantation procedure and may reduce the risk of error or injury.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the disclosed invention. For all the embodiments described above, the steps of the methods need not be performed sequentially. Thus, it is intended that the scope of the present invention herein disclosed should not be limited by the particular disclosed embodiments described above, but should be determined only by a fair reading of the claims that follow.

What is claimed is:

1. An instrument guide, comprising:
   a shaft having a proximal end and a distal end, wherein the distal end comprises a threaded surface;
   a handle attached to the proximal end of the shaft;
   a device coupler comprising a coupling base with a through lumen and an elongate coupling member comprising a proximal end and a distal end, wherein the distal end is configured with a least one mechanical interfit structure, wherein at least a portion of the elongate coupling member is configured so as to move in the through lumen of the coupling base; and
   at least one drill guide member joined to the device coupler;
   wherein the proximal end of the elongate coupling member of the device coupler, comprising a threaded surface complementary to the threaded surface of the distal end of the shaft, releasably locks to the distal end of the shaft.

2. The instrument guide as in claim 1, wherein the mechanical interfit structure comprises helical threads.

3. The instrument guide as in claim 1, further comprising at least one fixed coupling member extending from the coupling base.

4. The instrument guide as in claim 1, wherein the coupling base comprises a distal concave surface.

5. The instrument guide as in claim 1, further comprising a distal tubular shaft joined to the coupling base, the distal tubular shaft having a proximal end, a distal end and a lumen therebetween in which at least a portion of the elongate coupling member movably resides.

6. The instrument guide as in claim 5, wherein the elongate coupling member has a proximal position and a distal position.

7. The instrument guide as in claim 1, wherein the mechanical interfit structure comprises a hook that engages a recess or pin on an implantable device.

8. The instrument guide as in claim 1, wherein the mechanical interfit structure comprises a pivot or clamp member configured to grasp onto a side of an implantable device.

* * * * *

UNITED STATES PATENT AND TRADEMARK OFFICE
CERTIFICATE OF CORRECTION

| | | |
|---|---|---|
| PATENT NO. | : 8,764,762 B2 | Page 1 of 1 |
| APPLICATION NO. | : 13/426388 | |
| DATED | : July 1, 2014 | |
| INVENTOR(S) | : Jason Daniel Blain | |

It is certified that error appears in the above-identified patent and that said Letters Patent is hereby corrected as shown below:

Title Page (item 75, Inventors) line 1, Change "Encintas, CA" for Jason Blain to --Encinitas, CA--.

Title Page (item 75, Inventors) line 2, Change "Encintas, CA" for Greg Martin to --Encinitas, CA--.

In the Specification

Column 2 line 17, Change "a" to --at--.

In the Claims

Column 10 line 48, Claim 1, Change "a" to --at--.

Signed and Sealed this
Seventeenth Day of February, 2015

Michelle K. Lee
*Deputy Director of the United States Patent and Trademark Office*